Figure 1:
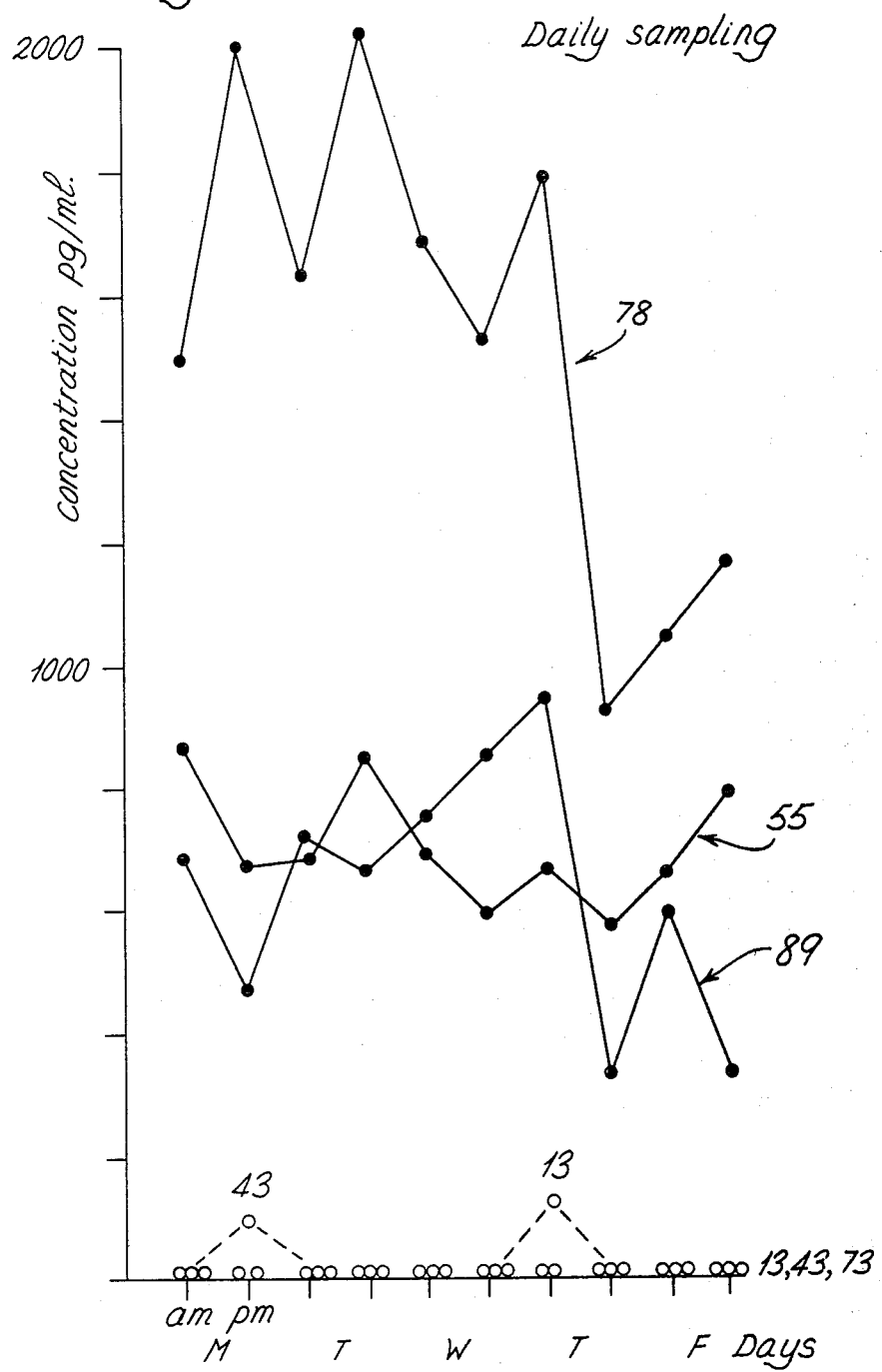

United States Patent [19]

Heap

[11] 4,294,922
[45] Oct. 13, 1981

[54] METHOD FOR MONITORING PREGNANCY IN MILK-PRODUCING DOMESTIC ANIMALS

[75] Inventor: Robert B. Heap, Cambridge, England

[73] Assignee: National Research Development Corporation, London, England

[21] Appl. No.: 105,604

[22] Filed: Dec. 20, 1979

[30] Foreign Application Priority Data

Dec. 29, 1978 [GB] United Kingdom ............... 50234/78

[51] Int. Cl.³ ......................... G01N 33/54; C12Q 1/44
[52] U.S. Cl. ............................................. 435/7; 435/19; 435/806; 424/8; 424/12; 23/230 B; 23/917
[58] Field of Search .............. 23/230 B, 917; 435/806, 435/7, 19, 810; 424/8, 12

[56] References Cited

U.S. PATENT DOCUMENTS

| | | | |
|---|---|---|---|
| 3,615,229 | 10/1971 | Bersh et al. | 23/917 |
| 3,826,616 | 7/1974 | Laing | 23/917 |
| 3,955,928 | 5/1976 | Yee | 23/230 B |
| 4,062,733 | 12/1977 | Edwards et al. | 23/230 B |
| 4,208,400 | 6/1980 | Edwards | 424/12 |

OTHER PUBLICATIONS

Richarson et al.; "Hormonal Substances in Human Milk, Cow's Milk and Dairy Products"; Jour. of Food Protection, vol. 40, No. 1, pp. 57-64, (1977).

*Primary Examiner*—Benoit Castel
*Attorney, Agent, or Firm*—Finnegan, Henderson, Farabow, Garrett & Dunner

[57] ABSTRACT

A method for monitoring pregnancy in a milk-producing domestic animal comprises determining the concentration of oestrogen conjugates, especially oestrone sulphate, contained in a sample comprising, or derived from, the milk of the animal and comparing this concentration with the average concentration of oestrogen conjugates in the milk of a non-pregnant similar animal of the same species. There is also provided a method for monitoring foetal well-being during the later stages of pregnancy which comprises, in addition, comparing the measured oestrogen conjugate concentration with that expected during a normal pregnancy.

17 Claims, 3 Drawing Figures

METHOD FOR MONITORING PREGNANCY IN MILK-PRODUCING DOMESTIC ANIMALS

This invention relates to a method for monitoring pregnancy in milk-producing domestic animals, and which advantageously also provides an indicator of foetal well-being during pregnancy.

For efficient husbandry of milk-producing domestic animals, such as goats and especially cattle, it is desirable to be able to routinely diagnose the instance of pregnancy and subsequently to monitor foetal well-being during pregnancy. Failure to detect unsuccessful insemination or subsequently loss of pregnancy, due to abortion or otherwise, not only disrupts the breeding programme but, with dairy animals, gives rise to undesirably prolonged loss of milk production. Traditionally, accurate diagnosis of pregnancy in such animals has depended on clinical examination by a skilled diagnostician, though recently the diagnostic test described in U.K. Patent Specification No. 1,402,263, which is based on the determination of the progesterone content of milk, has been widely adopted. This test is not completely satisfactory, however, as the progesterone which is determined is derived from the corpus luteum of the animal, and is secreted, not only as the result of conception, but also during the normal fertility cycle of the animal. Consequently the timing of the progesterone test, in relation to the supposed date of conception i.e. insemination, is highly critical and eccentricities in the fertility cycle of individual animals, let alone the normal luteal progesterone secretion of non-pregnant animals, can give rise to inaccuracies in the test.

A new diagnostic method has now been devised, based on the determination of oestrogen conjugates present in milk. These conjugates are metabolic products of oestrogens which in cows and goats are direct products of a conceptus, unlike progestogens, and are associated with the development of the endocrine properties of the placenta and thus presumably of a viable conceptus.

A recent review (Richardson and Mattarella, Journal of Food Protection (January 1977) Volume 40, Number 1, pages 57-64) concerning the measurement of hormonal substances in milk indicates extremely wide discrepancies between results obtained by different workers who have attempted to measure oestrogens and oestrogen conjugates in milk from pregnant and non-pregnant cows. These results, at best, tend to indicate that oestrogen conjugates would not be present in milk from pregnant animals at sufficient concentrations to permit measurement except by highly sophisticated, "research" techniques, and further that the differences in concentration of oestrogen conjugates between milk from pregnant and non-pregnant animals would not be sufficiently significant to provide the basis of a routine diagnostic test. It is thus surprising that it has now been found possible to routinely monitor pregnancy in milk-producing domestic animals by determining the concentration of oestrogen conjugates in milk.

Accordingly the present invention comprises a method for monitoring pregnancy in a milk-producing domestic animal in which the concentration of oestrogen conjugates contained in a sample comprising, or derived from the milk of the animal is determined and compared with the average concentration of oestrogen conjugates in the milk of a non-pregnant similar animal of the same species.

The method of the present invention may be used to monitor pregnancy in milk-producing domestic animals in general, including both meat-producing animals and dairy animals. Thus the method may be used for monitoring pregnancy in sheep and beef cattle, in as far as it is possible to obtain milk samples from such animals. More usually, however, the method is used for monitoring pregnancy in dairy animals, such as goats and especially dairy cows.

The method of the present invention may be carried out on any suitable milk based sample. Thus the sample may comprise an appropriate fraction or extract of the whole milk, and, in particular, it has been found to be desirable to carry out the method on a sample comprising the aqueous fraction of milk e.g. the whey fraction. It is envisaged, however, that the sample may advantageously comprise whole milk. Generally, it has been found that oestrogenic conjugates are stable to repeated cycles of freezing and thawing, and also it is not normally necessary to include preservatives or like substance in the milk if it is stored before applying the method of the invention.

The conjugates which are determined in the method of the invention are oestrogen conjugates in general, though preferably these are sulpho-conjugates, especially estrone sulphate. The concentration of these oestrogen conjugates may be determined by any suitable method. Thus in one embodiment the oestrogen conjugates are determined directly; for instance by an immuno-assay technique for determination of oestrogen conjugates e.g. oestrone sulphate. In an alternative embodiment, however, the sample is subjected to treatment to convert oestrogen conjugates contained therein to oestrogens, the concentration of which is then determined.

In this latter embodiment any suitable treatment may be used to convert oestrogenic conjugates to corresponding oestrogens, usually treatment to hydrolyse the conjugate to the corresponding oestrogen. Preferred treatment comprises enzymatic hydrolysis. Thus for example, the treatment comprises hydrolysis of sulpho-conjugates, preferably enzymic hydrolysis with a sulphatase enzyme, to yield the corresponding oestrogen, especially sulphatase hydrolysis of oestrone sulphate to oestrone. Any suitable sulphatase enzyme may be used, and, for the purposes of the present invention the sulphatase derived from the digestive juice of the snail, *Helix pomatia,* has been found to be eminently satisfactory.

Any suitable technique may be employed to determine the concentration of the oestrogens, usually oestrone, subsequent to the treatment, provided the technique is capable of detecting the concentrations involved e.g. concentrations of oestrone spanning the range from about 10 pg/ml up to about 2 ng/ml or more usually from about 100 or 200 pg/ml up to about 2 ng/ml. Prior to the determination the oestrogens may be extracted from the sample, preferably solvent extracted with a suitable non-polar organic solvent such as diethyl-ether; though preferably the oestrogens are determined within the original sample, without extraction. It will be appreciated, however, that if the sample is a sample of whole milk the oestrogens which are determined will be derived from both free and conjugated oestrogens and the value obtained will represent the total oestrogen content of the original milk sample. An immunoassay technique is preferably employed for the determination of the oestrogen concentration; for instance a radioimmunoassay technique or other immunoassay techniques, e.g. an enzyme-linked immunoassay technique, may be used.

Thus in one preferred embodiment the invention comprises a method for monitoring pregnancy in a milk-producing domestic animal, in which a sample comprising, or derived from, the milk of the animal is treated with a sulphatase enzyme so as to convert oestrone sulphate contained therein to oestrone, and in which the concentration of said oestrone is determined by an immunoassay technique.

Kits may be provided for carrying out the method of the invention, either by direct determination of oestrogen conjugates or determination of corresponding oestrogens after suitable treatment. Such kits typically comprise appropriate assay reagents characteristically in a form compatible with milk derived samples or especially milk. For example, the kit may comprise suitable immunoassay reagents for determination of oestrogen conjugates or oestrogens e.g. oestrone sulphate or oestrone, and in the latter case will usually also comprise enzyme e.g. sulphatase, for treating the sample so as to convert oestrogenic conjugates contained therein to corresponding oestrogens. The immunoassay reagents generally comprise suitable anti-serum and "known" quantities of appropriate oestrogen conjugates or oestrogens e.g. oestrone sulphate or oestrone. In a preferred form the kit is such that it is suitable for "on farm" use, and in this respect the assay technique used may be a suitable enzyme-labelled immunoassay in which the end point is determined colorimetrically e.g. by an easily discernible colour change. In an alternative embodiment the kit may be in a form suitable for use in a fluorescently or phosphorescently labelled immunoassay technique.

According to the present invention it has been discovered that the concentration of oestrone sulphate in bovine milk rises during gestation until lactation ceases. Small amounts of oestrone sulphate (e.g. about 150 pg/ml in oestrone equivalent) are detectable in bovine whey as early as days 40–60, and advantageously such amounts may be distinguished from the normal background quantities (e.g. about 30 pg/ml, in oestrone equivalent) in whey from non-pregnant animals, i.e. corresponding to the average concentration of oestrogen conjugates in the milk of a non-pregnant cow.

In some cases it has been found that, during the next 40 days (days 60–100), there is apparently a slight decline in concentration. Thereafter however, the concentration increases progressively (e.g. from about 100–200 pg/ml up to a maximum of about 1–2 ng/ml, in oestrone equivalent). It will be appreciated that the actual concentration of oestrogen conjugates present in the milk of both pregnant and non-pregnant animals may vary in accordance with specific breed of animal and fraction of milk which is sampled. Thus it may be expected that breeds of cattle having very high milk yields will produce milk which may contain comparatively low oestrogen conjugate concentrations due to a dilution effect, and that the first milk which is collected at the start of milking may contain comparatively higher oestrogen conjugate concentrations than subsequently collected milk in view of the comparatively lower fat content of the former.

Furthermore however, without prejudice to the foregoing, it is believed that the oestrogen conjugate concentration present in cows milk may pass through comparatively high levels during the period from about day 15 to about day 20 of pregnancy. It has been noticed recently in cows that the uterine blood flow to the uterine horn containing a pregnancy is markedly increased during the period from about day 15 to about day 20 of the pregnancy, and it is known that oestrogens stimulate blood flow. Thus if this transient increase in uterine blood flow is due to oestrogen secretion, it is believed that the milk oestrogen conjugate levels will be correspondingly increased. We also have recently discovered that milk oestrogen conjugate concentration is elevated at oestrus, and thus it is desirable to assay milk progesterone in parallel to avoid false positives.

Thus the method of the invention may be used as an early indicator of pregnancy after insemination; for instance, possibly during the period from about days 15–20, e.g. in parallel with the progesterone in milk assay, though more usually in the period days 40–60, e.g. about day 50 after the supposed date of conception, i.e. the date of artificial insemination or natural mating. In addition, however, the method of the invention may be used to diagnose pregnancy relatively later on during the gestation period, from about day 80 up to about day 120 or later, e.g. at about 100 days after conception and as such the method of the invention may advantageously provide a back-up pregnancy test to confirm the diagnosis of the progesterone assay which is normally carried out at a relatively early stage, e.g. 20–30 days or 40–70 days after insemination. Generally, however, the efficiency of diagnosis has been found to be best during this later period, e.g. 100% efficiencies being achieved after about day 100, whereas efficiency of 50–75% are achieved at about day 50.

Without prejudice to the generality of the present invention, it is believed that secretion of oestrone sulphate is indicative of a viable conceptus, and thus the method of the invention may be used to monitor foetal well-being in general, and in particular during the latter stages of pregnancy, e.g. after about day 100, by comparing the measured oestrogen conjugate concentration with that expected during a normal pregnancy. For instance, the method of the invention may be used to diagnose early embryonic death after a positive diagnosis by the progesterone test.

Figure 2:
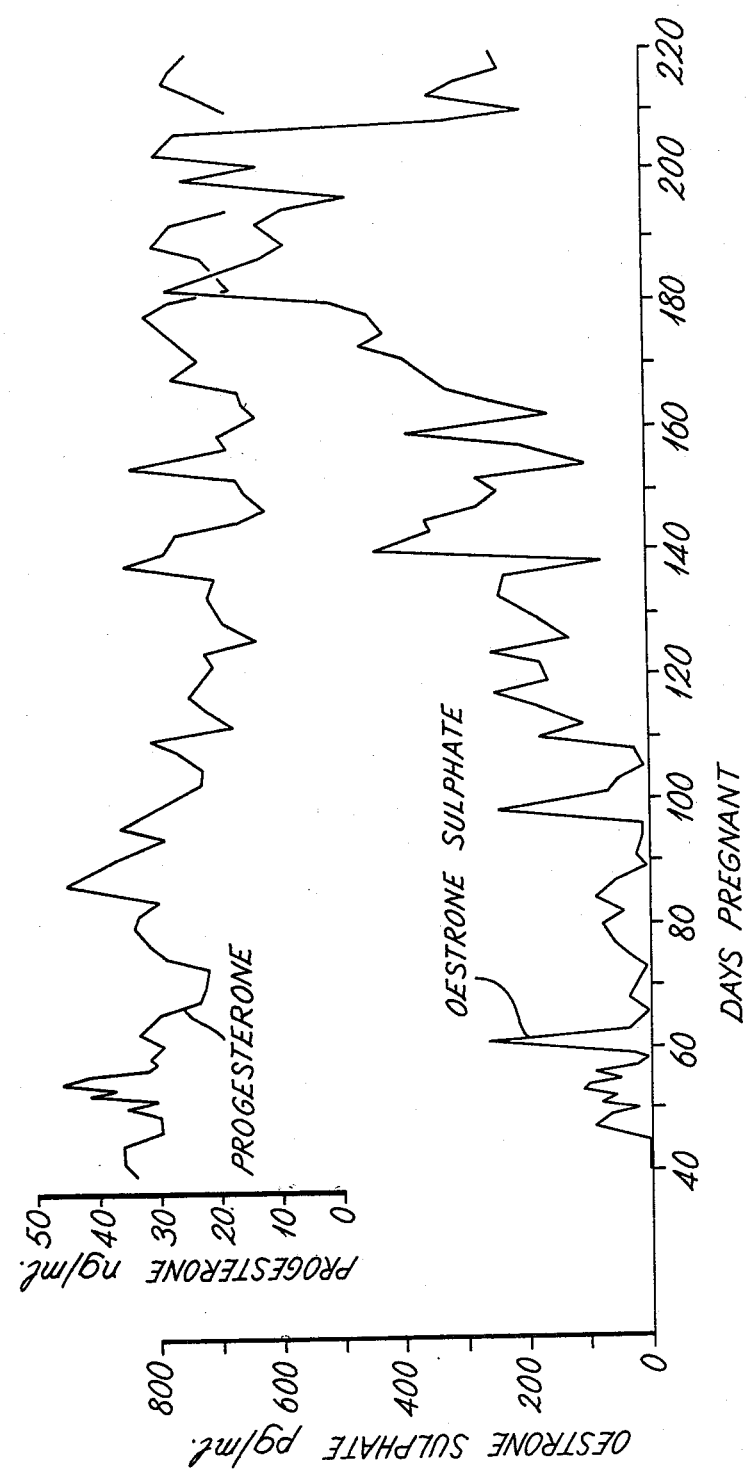
Figure 3:
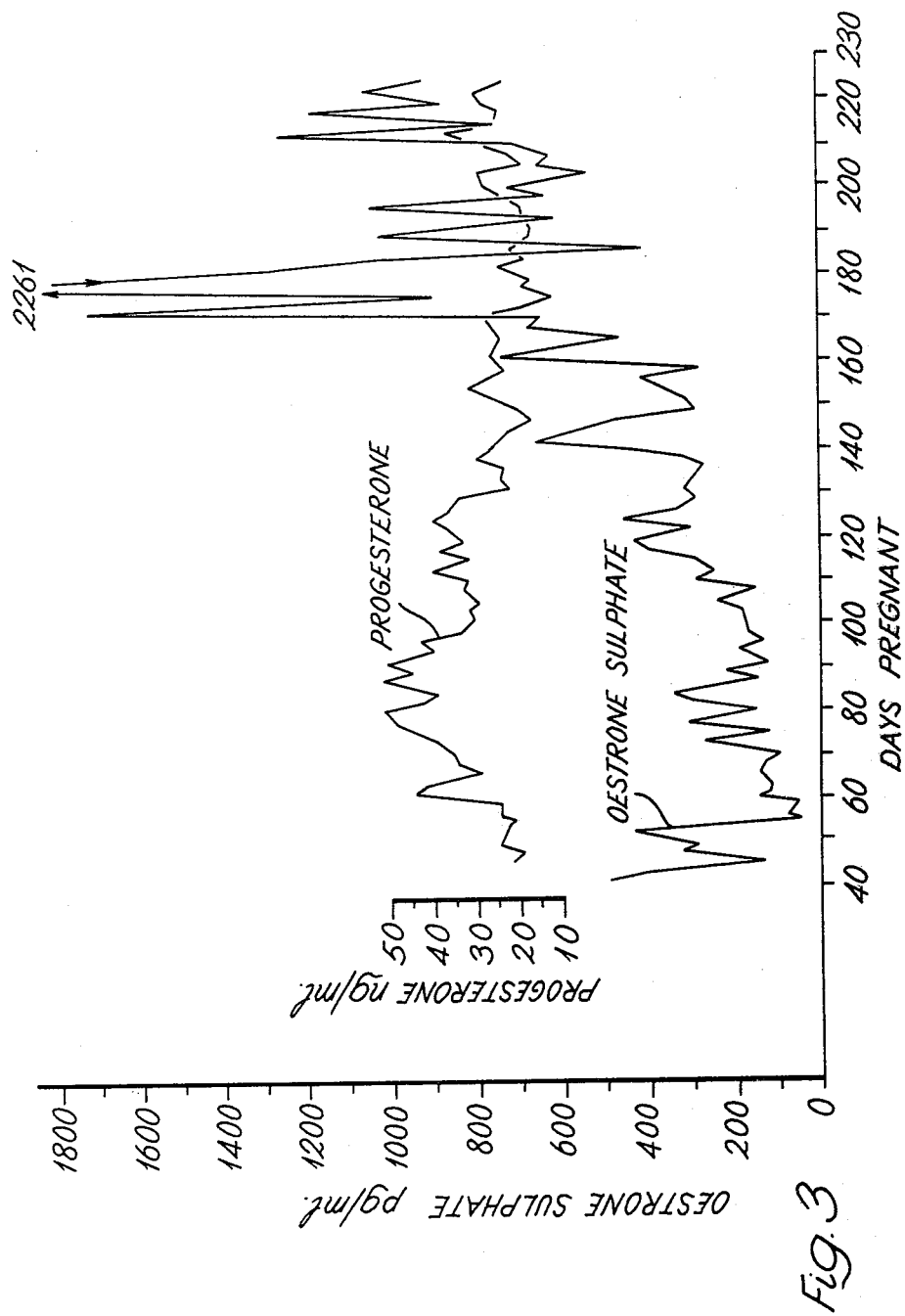

The following Examples are given to further illustrate the invention, Example 1 referring to FIG. 1 which is a graph showing the oestrone sulphate concentrations in milk for a group of 3 pregnant and 3 non-pregnant cows during the course of a normal week, and Example 4 referring to FIGS. 2 and 3 which are graphs showing the diurnal variations of the oestrone sulphate concentrations in milk from 2 cows over an extended period.

EXAMPLE 1

Milk samples were collected from two herds of cows, a herd of Jersey cows kept at the A.R.C. Institute of Animal Physiology, Brabraham, Cambridge, and a commercial herd of British Friesians, and the oestrone sulphate contents of samples was determined by the method of the invention.

Both herds of cows were milked twice-a-day, the milking routine consisting of udder wash with removal of first milk for the Jersey cows and a visual check for udder contamination in the case of the Friesian cows. During sampling, which was over a period of four autumn months, the animals were fed on a variety of diets, including grass supplemented with grass silage, green maize, grass nuts, hay and concentrates in the case of the Jerseys, and grass, hay, silage and concentrates in the case of the Friesians.

In the case of the Jersey cows pregnancy was diagnosed 60-90 days after insemination by physical examination, and in the case of the Friesians by milk progesterone assay at Day 24 confirmed subsequently by physical examination. Oestrus was recorded when mounting behaviour was observed.

SAMPLING PROCEDURE

Samples were obtained from animals during afternoon milking at various stages of the oestrus cycle and during gestation. Whole milk samples (20-30 ml) were taken in polypropylene bottles from the milk reservoir collected from each animal, and transferred to the laboratory at ambient temperature. Preservatives were not added to the milk samples as these had been found to have an adverse effect on the assay procedure subsequently to be carried out on the samples.

OESTRONE SULPHATE ASSAY

(i) Hydrolysis

Milk samples were centrifuged at 23,000 g for 30 min at 4° C. and the clear whey fraction removed. Whey, 100 μl, was pipetted in duplicate into acetone-rinsed bacteriological test tubes (126×155 mm), and 100 μl, of dilute enzyme solution (1 in 10 enzyme solution in acetate buffer, 0.2 M, pH 4.6) was added. The enzyme used was the sulphatase enzyme obtained from the whole digestive juice of the snail, *Helix pomatia*, supplied in sterile 1 ml ampoules by Uniscience Ltd., 8 Jesus Lane, Cambridge, U.K., and manufactured by L'Industria Biologique Francaise (activity per ampoule: sulphatase 80,000 U.F., and glucoronidase 10,000 U.F.). The diluted 1 in 10 enzyme solution was stable at 4° C. for about 1 week. After mixing, the tubes were incubated at 56° C. for 30 min., to complete hydrolysis of conjugated oestrogens. Control samples were run in parallel and consisted of 100 μl volumes of distilled water and acetate buffer (0.2 M, pH 4.6), or 100 μl volumes of distilled water and diluted enzyme solution. The efficiency of hydrolysis and extraction was determined by the addition of [$^3$H] oestrone sulphate, 7000 dpm/100 μl whey.

(ii) Extraction

After hydrolysis, double-distilled water (0.5 ml) and diethyl-ether (5 ml) was added to all tubes, the samples were mixed for 5 min, and then placed on solid $CO_2$ to freeze the aqueous phase. The ether phase was decanted, washed with 1 ml distilled water, mixed, and frozen again to remove the aqueous phase. The ether phase was decanted into bacteriological test tubes (75×12.5 mm) and evaporated to dryness under a stream of nitrogen at 50° C. on a water bath. The ether phase from tubes originally containing labelled oestrone sulphate was decanted into scintillation vials to determine the procedural losses, and radioactivity being determined after addition of 100 μl phosphate buffer (0.05 M, pH 7.4) and Fiscint scintillation fluid (PPO, 5 g. POPOP, 100 mg in 1 l toluene and 500 ml Fisons emulsifier) to compare with the amount of [$^3$H] oestrone sulphate added at the beginning of the procedure.

(iii) Radioimmunoassay

After hydrolysis and extraction of the sample 100 μl of antiserum (1 in 100,000 dilution) was added and after standing at room temperature for 30 min, 100 μl [$^3$H] oestrone is phosphate buffer (about 20,000 dpm/ml) was added to each tube. The tubes were agitated to mix their contents, incubated at 4° C. for 4-24 h, and 1 ml 0.25% dextran-coated charcoal (Heap et al 1976, Br. Vet. J. 132, 445-464) was added. After mixing the samples were incubated for 5-10 min at 4° C., centrifuged at 800 g for 10 min at 4° C., and the supernatant decanted. Radioactivity of the samples was then determined after addition of toluene—PPO scintillation fluid. A calibration curve was also prepared for each assay using triplicate amounts of 10 μl of 0, 1.25, 2.5, 5.0, 10, 25 and 50 ng/ml of oestrone in redistilled ethanol, the standards being evaporated to dryness and treated in an identical manner to the samples.

The calibration curve was fitted by computer to a weighted asymptotic or hyperbolic model as described by Walters 1974, Applied Statistics, 23, page 43 and the sample concentrations were calculated as the mean of duplicates (pg/ml, with standard error) by interpolation. The values are expressed as oestrone equivalents and the conversion factor to obtain gravimetric amounts of oestrone sulphate is 1.4.

For radioimmunoassay of oestrogens, anti-serum BF 461 No. 6 was used, having been raised in a goat immunized against oestradiol-17 β-hemisuccinyl-bovine serum albumin and cross-reacted with oestrone (100%), oestradiol-17 β (110), oestradiol-17 α (8.0), oestriol, epi-oestriol, 16α-hydroxyoestrone, 2-methoxyoestradiol-17β, 2-methoxyoestrone, 16-oxo-oestradiol-17β, testosterone, androstenedione and progesterone (<1.0). A specific anti-serum against oestradiol-17β, BF 510 No. 5 was also used, being raised in a goat immunized against oestradiol-6-carboxyoxime-bovine serum albumin and cross-reacted with oestradiol-17 β (100), testosterone (1.2), oestrone (0.7), epi-oestriol (0.3), oestradiol-17α, oestriol, 16α-hydroxyoestrone, 2-methoxyoestradiol-17β, 2-methoxyoestrone, 16-oxo-oestradiol-17β, androstenedione and progestrone (0.1).

RESULTS

Distribution of oestrone sulphate in milk

Table 1 below shows the distribution of [$^3$H] oestrone sulphate (2μ Ci) added to 10 ml whole milk after 18h at 4° C. In milk from pregnant and non-pregnant animals 83.5 and 91.0%, respectively, of the radioactivity was recovered in the whey fraction.

TABLE 1

Distribution of oestrone sulphate in milk after the addition of [$^3$H] oestrone sulphate.

| Milk fraction | % Recovery | |
|---|---|---|
| | Non-pregnant | Pregnant |
| Whey | 91.0 | 83.5 |
| Fat | 4.3 | 4.2 |
| Casein | 5.2 | 6.8 |

ASSAY EVALUATION

The overall recovery of [$^3$H] oestrone sulphate added to whey was 79.0±0.56% (51 observations) and values are corrected for this procedural loss. The reagent blank value of the assay was 27.9±1.9 pg per tube (23), and the blank value for whey obtained from non-pregnant animals was 29.9±9.5 (29 observations, Jerseys) and 35.7±12.7 (37 observations, Friesians). The coefficient of variation within assays was 19.1% in the concentration range 100-1200 pg/ml. Addition of known amounts of authentic oestrone sulphate to 100 μl whey aliquots gave the following results: 0 (added), 360 pg/ml (measured); 1000, 1090; 2000, 1710; 3000, 2870.

The results given in Table 2 below show that there was no significant difference in the whey concentration of oestrone sulphate between samples assayed immediately after collection or after repeated freezing and thawing.

TABLE 2

Effect of storage on oestrone sulphate concentrations in whey of Jersey cows (pg/ml, means ± S.E.M.)

| Cow No. | Fresh whey | After storage[a] |
|---|---|---|
| 90 | 490 ± 20 | 534 ± 47[b] |
| 78 | 1020 ± 70 | 1120 ± 116 |
| 89 | 700 ± 50 | 732 ± 114 |
| 86 | 865 ± 125 | 1048 ± 128 |
| 55 | 370 ± 50 | 446 ± 97 |
| 41 | 510 ± 40 | 448 ± 71 |
| 93 | 515 ± 135 | 600 ± 71 |

[a]Mean value for samples frozen and thawed before assay on four occasions, total period of storage 8 days.
[b]Paired t-test, no significant difference between any samples.

To investigate the nature of the oestrogens in whey, samples were examined in three assays. Samples were hydrolysed and extracted to give total unconjugated and conjugated oestrogens; samples were extracted with ether alone to give total unconjugated oestrogens; and samples were extracted to remove unconjugated oestrogens and the remainder hydrolysed to give conjugated oestrogens. The results obtained are given in Table 3 below and show that in all animals unconjugated and conjugated oestrogens were detected in whey, but in pregnant cows the value of conjugated oestrogens was much higher than in non-pregnant animals whereas the value of unconjugated oestrogens remained about the same.

TABLE 3

Concentration of unconjugated and conjugated oestrogens in whey of non-pregnant and pregnant cows (means of duplicates)

| Cow No. | Condition | Concentration (pg/ml) | | |
|---|---|---|---|---|
| | | Unconjugated | Conjugated | Total |
| R23 | Not pregnant | 130 | 0 | 130 |
| 71 | Not pregnant | 40 | 170 | 290 |
| 75 | Not pregnant | 70 | 80 | 110 |
| 89 | Pregnant, 193d | 20 | 390 | 850 |
| 78 | Pregnant, 194d | 70 | 570 | 850 |
| 86 | Pregnant, 200d | 150 | 800 | 1130 |
| 2 | Pregnant, 238d | 70 | 2990 | 3050 |

The identification of oestrogens in whey was further investigated using the highly-specific anti-serum against oestradiol-17β. The majority of activity cross-reacted with the anti-serum raised against oestrone and there was relatively little activity associated with oestradiol-17β.

OESTRONE SULPHATE CONCENTRATIONS IN WHEY DURING PREGNANCY

Table 4 shows the whey concentration of oestrone sulphate in the Institute's herd of Jersey cows. The concentration increased to reach a peak between days 41–60 after insemination (151±50.2 pg/ml), and after a slight decline during the next 40 days, it increased progressively between days 100–200. Maxmium values of about 1 ng/ml were obtained after about day 180. A similar pattern occurred in the Friesian herd.

TABLE 4

Oestrone sulphate concentration (in oestrone equivalent, mean ± S.E.M.) in whey during pregnancy.

| Days pregnant | No. of animals | Concentration pg/ml |
|---|---|---|
| 0–20[a] | 9 | 38 ± 23 |
| 21–40 | 11 | 66 ± 18 |
| 41–60 | 8 | 151 ± 50 |
| 61–80 | 9 | 99 ± 39 |
| 81–100 | 7 | 93 ± 41 |
| 101–120 | 5 | 118 ± 73 |
| 121–140 | 3 | 234 ± 80 |
| 141–160 | 5 | 350 ± 77 |
| 161–180 | 5 | 537 ± 187 |
| 181–200 | 9 | 799 ± 169 |
| 201–220 | 7 | 698 ± 82 |
| 221–240 | 4 | 967 ± 177 |
| Not pregnant | 29 | 30 ± 10 |

[a]Values between 0–140 days contain animals in which pregnancy has been assumed from non-return to service.

The accompanying diagram gives, in graph form, the results obtained, when the oestrone sulphate concentration was determined in the milk of 3 non-pregnant (designated as cows 13, 43 and 73) and 3 pregnant (designated as cows 55, 78 and 89) cows during the course of a normal working week, using the method of the invention as described above. The values obtained for the oestrone sulphate concentrations were consistently higher in the pregnant as compared with the non-pregnant animals.

EXAMPLE 2

The oestrone sulphate concentration was determined in a group of six pregnant cows (designated as cows 1 to 6), which were at varying stages of pregnancy ranging from 53 days to 200 days, using an adaptation of the method described in detail in Example 1. The method used was substantially the same as that used in Example 1, with the exception, however, that the oestrone was not extracted from the whey and the radioimmunoassay was carried out directly on whey samples. The results obtained are given below in Table 5, which includes a figure of 0 obtained for the milk of a non-pregnant cow by the adapted method.

TABLE 5

Oestrone sulphate concentration (in oestrone equivalent) in the whey of a group of 6 pregnant cows at various stages of pregnancy by direct method, without extraction from whey.

| Cow No. | Days pregnant | Concentration pg/ml whey |
|---|---|---|
| 1 | 53 | 325 |
| 2 | 73 | 190 |
| 3 | 74 | 535 |
| 4 | 175 | 400 |
| 5 | 181 | 725 |
| 6 | 200 | 1875 |
| Non-pregnant | | 0 |

EXAMPLE 3

Further to the results given in Table 4, Example 1, anomalous behaviour was noticed in three animals which were previously assumed to be normally pregnant on the basis of clinical examination 60–90 days after insemination. It became apparent, however, that pregnancy had failed mid-term in two of the cows 95 and 6, whereas in the case of the third cow calf birth weight was unusually low (15.9 kg compared with a normal range of 25–30 kg). Oestrone sulphate determinations carried out on the whey of the former two animals indicated that pregnancy had failed at about 170 and 90 days when levels were found to be about 30% of normal. The results obtained for oestrone sulphate determinations for these two animals are given below in Table 6.

TABLE 6

Oestrone sulphate in whey in 2 cows showing mid-term pregnancy loss.

| Animal No. | Stage (days) | Oestrone sulphate concentration (pg/ml) | |
|---|---|---|---|
| | | Observed | Expected (mean ± S.E.) |
| 95 | 130 | 150 | 234 ± 80 |
| | 150 | 240 | 350 ± 77 |
| | 172 | 37 | 537 ± 187 |
| | 194* | 56 | 799 ± 169 |
| | 213 | 0 | 698 ± 82 |
| 6 | 42 | 0 | 151 ± 50 |
| | 62 | 240 | 99 ± 39 |
| | 84 | 30 | 93 ± 41 |
| | 106 | 0 | 118 ± 73 |
| | 125 | 161 | 234 ± 80 |
| | 167 | Return to oestrus | |

*Assumed pregnant by experienced stockman, failed to produce calf at 280-290 days, and subsequently oestrus induced by prostaglandin treatment.

Oestrone sulphate determinations carried out on the animal that produced a small calf indicated concentrations in whey which were much lower than normal after about 170 days, the time when foetal growth is known to increase markedly. The results obtained for oestrone sulphate determinations carried out on whey samples from this animal are given below in Table 7.

TABLE 7

Oestrone sulphate in whey and foetal size.

| Animal No. | Stage (days) | Oestrone sulphate concentration (pg/ml) | |
|---|---|---|---|
| | | Observed | Expected (means ± S.E.) |
| 75 | 1 | 40 | 38 ± 23 |
| | 17 | 0 | 38 ± 23 |
| | 39 | 54 | 66 ± 18 |
| | 55 | 35 | 151 ± 50 |
| | 75 | 253 | 99 ± 39 |
| | 95 | 720 | 93 ± 41 |
| | 114 | 520 | 118 ± 73 |
| | 135 | 360 | 234 ± 80 |
| | 156 | 364 | 350 ± 77 |
| | 174 | 299 | 537 ± 187 |
| | 195 | 102 | 799 ± 169 |

EXAMPLE 4

In a further extension of the experiments described in previous Examples, frequent sampling of individual animals was adopted to determine in greater detail the pattern of oestrone sulphate secretion in milk and its diurnal variation. The results obtained for two animals (designated cows 2 and 14) over the periods from day 40-230 of pregnancy are given in FIGS. 2 and 3 showing that the oestrone sulphate concentration increased progressively over this period but that there were marked diurnal variations in both animals. Similar diurnal variations were not observed in milk progesterone tests carried out in parallel on these animals. The onset of oestrone sulphate concentration was well advanced in cow 14 by day 40 after conception, (see FIG. 3), but was delayed in cow 2 (see FIG. 2).

EXAMPLE 5

A field trial was conducted to determine the optimum sampling time for pregnancy diagnosis under field conditions.

Milk was sampled three times a week from a commercial herd of 39 high yielding Friesian cows during the period 40-100 days after conception. Samples were taken from whole milk collected from each animal at afternoon milking and either the whey was separated immediately before cold storage or the milk was stored at 4° C. before subsequent whey separation. The results obtained are given below in Tables 8 and 9, indicating comparatively low concentrations during the early stages due to a dilution effect as a result of the high milk yields of these animals. The optimal sampling time occurred between days 90-100 (see Table 9)

TABLE 8

Concentrations of oestrone sulphate in whey (Friesians)

| Days pregnant | Oestrone sulphate concentration (pg/ml) |
|---|---|
| 39-45 | 48.3 ± 6.57[a] (93)[b] |
| 46-50 | 47.1 ± 9.76 (68) |
| 51-55 | 36.7 ± 6.98 (69) |
| 56-60 | 46.5 ± 13.31 (79) |
| 61-65 | 63.9 ± 21.08 (23) |
| 66-70 | 46.7 ± 13.41 (27) |
| 71-75 | 67.2 ± 29.54 (19) |
| 76-80 | 29.4 ± 7.73 (25) |
| 81-85 | 86.1 ± 34.59 (24) |
| 86-90 | 56.3 ± 22.55 (20) |
| 91-95 | 110.3 ± 20.98 (23) |
| 96-100 | 66.2 ± 14.34 (24) |
| 100-105 | 111.5 ± 18.50 (18) |

[a] man ± S.E.
[b] number of animals

TABLE 9

Incidence of positive oestrone sulphate levels in whey (Friesians)

| Days pregnant | No. of animals | Number Positive | Number Negative | % |
|---|---|---|---|---|
| 39-45 | 93 | 62 | 31 | 66.6 |
| 46-50 | 68 | 46 | 23 | 66.2 |
| 51-55 | 69 | 41 | 28 | 59.4 |
| 56-60 | 79 | 40 | 39 | 50.6 |
| 61-65 | 23 | 16 | 7 | 69.6 |
| 66-70 | 27 | 22 | 5 | 81.5 |
| 71-75 | 19 | 15 | 4 | 78.9 |
| 76-80 | 25 | 17 | 8 | 68.0 |
| 81-85 | 23 | 14 | 9 | 60.9 |
| 86-90 | 20 | 10 | 10 | 50.0 |
| 91-95 | 23 | 21 | 2 | 91.3 |
| 96-100 | 23 | 19 | 4 | 82.6 |
| 100-105 | 18 | 18 | 0 | 100.0 |

I claim:

1. A method for diagnosing pregnancy in a milk-producing domestic animal, comprising determining the concentration of oestrogen conjugates contained in a sample comprising whole milk or a fraction thereof of the animal and comparing said concentration with the average concentration of oestrogen conjugates in the milk of a non-pregnant similar animal of the same species, whereby a significantly higher concentration in said sample than said average concentration indicates that said animal is pregnant.

2. A method for monitoring foetal well-being in a milk-producing domestic animal previously determined to be pregnant, comprising determining the concentration of oestrogen conjugates contained in a sample comprising whole milk or a fraction thereof of the animal previously determined to be pregnant and comparing the measured oestrogen conjugate concentration with that expected during a normal pregnancy, whereby a significantly lower concentration in said sample than that expected during a normal pregnancy contradicts foetal well-being.

3. A method according to claim 1 or 2, in which the concentration of oestrogen conjugates is determined in the whey fraction of the milk.

4. A method according to claim 1 or 2, in which the oestrogen conjugates which are determined are oestrogen sulpho-conjugates.

5. A method according to claim 4, in which oestrone sulphate is determined.

6. A method according to claim 1 or 2, in which the oestrogen conjugates are determined directly.

7. A method according to claim 1 or 2, wherein said step of determining the concentration of oestrogen conjugates comprises subjecting said sample to treatment to convert oestrogen conjugates contained therein to oestrogens, and then determining the concentration of the oestrogens.

8. A method according to claim 7, in which the treatment used to convert oestrogen conjugates to oestrogens comprises enzymatic hydrolysis.

9. A method according to claim 8, in which said enzymatic hydrolysis comprises treatment with a sulphatase.

10. A method according to claim 1 or 2, further comprising, prior to said determination, extracting the oestrogens from said sample.

11. A method according to claim 1 or 2, in which said determination of oestrogen conjugates comprises an immunoassay technique.

12. A method according to claim 1, comprising performing said diagnosis of pregnancy during the period from about 15 up to about 20 days after insemination.

13. A method according to claim 1, comprising performing said diagnosis of pregnancy during the period from 40-60 days after insemination.

14. A method according to claim 1, comprising performing said diagnosis of pregnancy during the period from about 80 to about 120 days after insemination.

15. A method according to claim 1, comprising performing said diagnosis of pregnancy during the period subsequent to about 120 days after insemination.

16. A method according to claim 15, comprising performing said monitoring foetal well-being during the later stages of pregnancy.

17. A method according to claim 16, wherein said monitoring foetal well-being occurs after about day 100 of pregnancy.

* * * * *